United States Patent [19]

Lahav et al.

[11] Patent Number: 4,533,506

[45] Date of Patent: Aug. 6, 1985

[54] RESOLUTION OF AMINO ACIDS

[75] Inventors: Meir Lahav; Lia Addadi; Isabela Weissbuch, all of Rehovot, Israel

[73] Assignee: Yeda Research and Development Company Ltd., Rehovot, Israel

[21] Appl. No.: 455,333

[22] Filed: Jan. 3, 1983

Related U.S. Application Data

[63] Continuation of Ser. No. 268,804, Jun. 1, 1981, Pat. No. 4,390,722.

[30] Foreign Application Priority Data

Jun. 8, 1980 [IL] Israel ........................................ 60254

[51] Int. Cl.$^3$ .............................................. C07B 19/00
[52] U.S. Cl. .................................. 260/501.12; 562/402
[58] Field of Search .................... 260/501.12; 562/402

[56] References Cited

U.S. PATENT DOCUMENTS

| | | | |
|---|---|---|---|
| 2,790,001 | 4/1957 | Purvis ................................. | 562/402 |
| 2,940,998 | 6/1960 | Ogawa et al. ....................... | 562/402 |
| 3,660,474 | 5/1972 | Chibata et al. ..................... | 562/402 |
| 3,933,902 | 1/1976 | Watanabe et al. ................. | 260/501.12 |
| 4,390,722 | 6/1983 | Lahav et al. ........................ | 562/402 |

*Primary Examiner*—Natalie Trousof
*Assistant Examiner*—Vera C. Clarke
*Attorney, Agent, or Firm*—Browdy and Neimark

[57] ABSTRACT

A process for resolution of a mixture of D- and L-amino acids, selected from threonine (THR), asparagine (ASN), p-hydroxyphenylglycine p-toluene sulfonate (pHPGpTS) and glutamic acid hydrochloride (GLU), which crystallize in the form of a conglomerate, whereby the ratio of one desired enantiomorph to the other undesired enantiomorph of said amino acid is increased in the crystalline compound obtained, as compared to the ratio in the starting material, which process comprises forming a supersaturated solution of said mixture, adding another predetermined amino acid as additive, which has a molecular structure which resembles that of one of the enantiomers of said racemic mixture, said additive being a D-amino acid as an inhibitor of the growing D-amino acid when the L-amino acid is desired, or a L-amino acid when the D-amino acid is desired, and crystallizing part of the compound from said supersaturated solution. When GLU.HCl is resolved, the crystals can be separated as they have different morphological forms.

8 Claims, No Drawings

RESOLUTION OF AMINO ACIDS

This is a continuation of application Ser. No. 268,804 filed June 1, 1981, now U.S. Pat. No. 4,390,722.

The present invention relates to a novel process for the resolution of amino acids from mixtures of the D- and L-forms, by crystallization from supersaturated solutions, in the presence of an additive, which results in the preferred crystallization of a predetermined desired form, in preference to the other. This can be considered as application of the kinetic resolution of racemates crystallizing in the form of conglomerates by carrying out the crystallization in the presence of small amounts of resolved additives, the stereochemical molecular structure of which resembles that of one of the enantiomers of the said racemic mixture.

This invention relates to the application of a similar principle to the resolution of four amino acids: threonine (THR), asparagine (which crystallizes from water as its monohydrate) (ASN), p-hydroxyphenylglycine-p-toluene sulfonate (pHPGpTS) and glutamic acid as its hydrochloride (GLU.HCl). Racemic mixtures of all four crystallize in the form of conglomerates.

It is known that all of the above compounds can be resolved by bringing aqueous solutions of their racemic mixtures to conditions of supersaturation, and then inducing preferential crystallization of the desired enantiomer by introducing seed crystals of this enantiomer. The invention described herein is based on a different principle.

We have found that addition of D-glutamic acid (D-GLU), D-asparagine (D-ASN), D-aspartic acid (D-ASP), or D-cysteine (D-CYS), or D-glutamine (D-GLN) in small amounts to a supersaturated solution of threonine in water brings about a preferred crystallization of the threonine in its L-form. Similarly, inclusion of the L-forms of the above additives leads to preferred crystallization of D-threonine. Further, we have found that from a supersaturated aqueous solution of D,L-asparagine, on addition of D-aspartic acid, D-glutamic acid of D-glutamine, there results a preferred crystallization of L-asparagine monohydrate; inclusion of the L-additives leads to preferred crystallization of D-asparagine monohydrate. Further, we have found that addition of L-tyrosine (TYR), L-tyrosine-p-toluene sulfonate (TpTS), L-dopa, L-dopa-p-toluene sulfonate (DpTS), L-α-methyl dopa, L-α-methyl dopa-p-toluene sulfonate (MDpTS), L-phenylalanine (PHE), L-phenylalanine-p-toluene sulfonate (PpTS), L-phenyl glycine (PG), L-phenyl glycine p-toluene sulfonate (PGpTS), L-p-methoxy phenyl glycine (pMPG) or L-p-methoxy phenyl glycine p-toluene sulfonate (pMPGpTS) to a supersaturated solution of pHPGpTS in an 0.5N aqueous solution of p-toluene sulfonic acid causes preferred precipitation of the D-form of pHPGpTS. On acidification the corresponding enantiomer of p-hydroxyphenylglycine can be obtained. Inclusion of the D-additives causes preferred precipitation of the L-form of pHPGpTS.

We have found that addition of D-lysine.HCl or D-lysine (D-LYS) D-ornithine.HCl or D-ornithine (D-ORN), or D-histidine.HCl or D histidine (D-HIS) in small amounts to a supersaturated solution of D,L-GLU in 5N HCl, brings about preferential crystallization of GLU in its L form in high enantiomerical purity. Furthermore the addition of D-serine (D-SER), D-threonine (D-THR), D-cysteine.HCl (D-CYS.HCl) in amounts larger than 20% of the amount of D,L-GLU to the supersaturated solution, brings about as well preferential crystallization of L-GLU.

Similarly, addition of the L-forms of the above additives leads to preferred crystallization of D-GLU.HCl.

In all the above cases, relating to glutamic acid, the enantiomer crystallizing first (of absolute configuration opposite to that of the additive), appears in the form of big well shaped bars and is contaminated by amounts lower than 0.1% of the additive, which can be removed by washing the crystal with solvent. The antipode can be obtained in the form of thin plates or powder by further crystallization of the residual mother liquor, and contains about 0.5% of the additive.

Alternatively, from extensive crystallization of the supersaturated solution the two morphological forms, namely bars and plates, can be obtained together and then mechanically separated, leading to resolution of the enantiomers of GLU.HCl.

In all the above cases crystals enriched in the second enantiomer can be obtained by crystallization from the residual mother-liquor, after separation of the first batch of crystals of the enantiomerically enriched product.

DETAILED DESCRIPTION

This invention can be used to produce crystalline threonine, asparagine monohydrate, pHPGpTS and glutamic acid, enriched in the desired enantiomer, without requiring the use of seed crystals of this enantiomer. The use of seed crystals from this enantiomer or from the racemic mixture may, however, be desirable from the point of view of the rate of crystallization.

For the case where a seed crystal of the desired enantiomer is used, this invention describes an improvement of the resolution process for threonine, asparagine, pHPGpTS, and glutamic acid HCl by further addition in solution of the appropriate additives for each amino acid as mentioned above.

The examples which follow are illustrative of the present invention but are not to be interpreted in a limiting sense.

EXAMPLE 1

Threonine 300 mg DL-threonine and 30 mg D-glutamic acid (i.e., 10% based on the mixture of D,L-threonine) were slurried in 1 cc H$_2$O, and heated to about 80° C. until complete dissolution occurred. The hot solution was filtered and cooled to room temperature without agitation. After 40 hrs 53 mg of crystals had formed, and these were separated by filtration. The specific rotation of these product crystals was $[\alpha]_D^{20} = -25.6$ (c5, H$_2$O), corresponding to an enantiomeric excess (e.e.) of 91% L-threonine in the crystals in a yield of 18% with respect to the initial D,L-threonine introduced. The crystals contain less than 1% D-GLU (high performance liquid chromatography). A second filtration of the mother liquors, after three days, gave 50 mg of crystals having $[\alpha]_D^{20} = +25.4$ (c5, H$_2$O), corresponding to 91% e.e. of D-THR in a yield of 17%.

EXAMPLE 2

Threonine

The solution of D,L-threonine and D-glutamic acid, prepared as in Example 1, was thermostated at 67° C. for 30 min, after which powdered crystals of L-THR (15 mg, 5%) were added and the resultant slurry was transferred to a thermostat at 25° C. where it was shaken for 60 min. Crystals (59 mg) separated and were filtered off; they had $[\alpha]_D^{20} = -27.1$ (c2, H$_2$O), corresponding to an e.e. of 94.8% of L-THR in the precipitated material (crystals additional to the seeds), in a yield of 14.6%.

EXAMPLE 3-8

Threonine

In a manner similar to examples 1 and 2, experiments were performed also at room temperature with 300 mg D,L-THR/c.c. H$_2$O, and with other additives. The conditions and results are given in Table I below. In examples 7 and 8 the crystallizations were performed with shaking, in examples 3-6 without.

TABLE I

Resolution of threonine in the presence of various additives

| Example | Additive | Weight % Additive* | Seed L-THR | Time (hr) | Precipitated Product e.e. THR (%) | Yield (%) |
|---|---|---|---|---|---|---|
| 3 | D-ASN | 10 | None | 40 | 90 L | 16 |
| 4 | D-ASP | 10 | none | 40 | 70 L | 16 |
| 5 | L-GLN | 10 | none | 40 | 90 D | 15 |
| 6 | L-CYS | 13 | none | 40 | 93 D | 7 |
| 7 | None | — | 5% | 1 | 5.5 L | 29.7 |
| 8 | D-GLU | 10 | 5% | 2 | 94.4 L | 14.8 |

*relative to D,L-THR.

EXAMPLE 9

Asparagine 300 mg D,L-asparagine. H$_2$O and 20 mg D-aspartic acid (i.e., 6.5% based on the mixture of D,L-asparagine.H$_2$O) were slurried in 3 cc H$_2$O and the slurry heated to about 80° C. until complete dissolution occurred. The hot solution was filtered and cooled to room temperature without agitation. After 100 hr the separated crystals (49 mg) were recovered by filtration, and had $[\alpha]_D^{20} = +24$ (c4, HCl 5N) corresponding to an e.e. of 79% of L-ASN in the crystals in a yield of 16%. The filtered crystals contained 1.2% D-ASP.

EXAMPLE 10

Asparagine 300 mg D,L-ASN.H$_2$O and 50 mg L-ASP were processed as in example 9. To the filtered, cool solution (supersaturated) was added 0.5 mg of crystalline, powdered D,L-ASN.H$_2$O.

After 20 hr 42 mg of crystals were recovered by filtration, and had $[\alpha]_D^{20} = -29.9$ (c4, HCl 5N) corresponding to an e.e. of 98% of D-ASN in the crystals in a yield of 14%.

EXAMPLES 11-14

Asparagine

In a manner similar to example 9, experiments were performed, also at room temperature and with 100 mg D,L-ASN.H$_2$O/cc water, with other impurities. The conditions and results are summarized in Table II.

TABLE II

Resolution of asparagine in the presence of various additives

| Example | Additive | Weight % Additive* | Time (hr) | Precipitated Product e.e. ASN (%) | Yield % |
|---|---|---|---|---|---|
| 11 | L-GLU | 15 | 90 | 85 D | 22 |
| 12 | L-GLN | 15 | 17 | 10 D | 35 |
| 13 | D-GLU | 15 | 90 | 79 L | 14 |
| 14 | none | 15 | 48 | 0 | 42 |

*relative to D,L-ASN.H$_2$O.

EXAMPLE 15 pHPGpTS 300 mg D,L-pHPGpTS and 22 mg L-tyrosine were slurried in 1 cc 0.5M p-toluenesulfonic acid (i.e., 7.3% based on the mixture of D,L-pHPGpTS) in water, and the slurry was heated until complete solution occurred. The hot solution was filtered and allowed to cool to room temperature without agitation. After 5 hr spontaneous crystallization started. After an additional 1.5 hr, 57 mg of crystals of pHPGpTS were collected by filtration; they had $[\alpha]_D^{20} = -50.5$ (c2, H$_2$O) corresponding to an e.e. of 75% of D-pHPGpTS in 19% yield. The crystals contained only traces of L-TYR.

EXAMPLE 16 pHPGpTS

The initial solution was made up as in example 15, and seeded at 30° with 1.5 mg (D-pHPGpTS (0.5%). The slurry was held at 30° C. in a thermostat, with gentle shaking. After 1 hr, 17.27 mg of crystals were collected by filtration, with $[\alpha]_D^{20} = -66.5$, corresponding to an e.e. of 98.7% of D-pHPGpTS in 5.3% yield.

EXAMPLES 17-21 pHPGpTS

In a manner similar to example 16, experiments were performed with different additives and conditions. The results are summarized in Table III below. In all cases the amount of seeds of D- or D,L-pHPGpTS was 0.5 weight % of the initial D,L-pHPGpTS. The additive was always 15 weight % of the initial D,L-pHPG.

TABLE III

Resolution of pHPGpTS in the presence of various additives

| Example | [D,L-pHPGpTS] (mg/cc) | Additive | Conditions* | Time (min.) | Purified Product c.c. (%) | Yield (%) |
|---|---|---|---|---|---|---|
| 17 | 350 | L-TYR | D-seeds at 50° C. followed by shaking at 30° C. | 120 | 61.4 | 24.5 |
| 18 | 350 | L-TYR | D-seeds at 50° C. followed by shaking at 25° C. | 60 | 100 | 5.3 |
| 19 | 300 | L-DOPA | D,L-seeds at 30° C. standing at 20° C. | 90 | 19.7 | 31.8 |
| 20 | 300 | L-PHE | as above | 90 | 31.3 | 20.8 |

TABLE III-continued

Resolution of pHPGpTS in the presence of various additives

| Example | [D,L-pHPGpTS] (mg/cc) | Additive | Conditions* | Time (min.) | Purified Product c.c. (%) | Yield (%) |
|---|---|---|---|---|---|---|
| 21 | 300 | L-MeDOPA | as above | 90 | 19.3 | 33 |

*D-seeds obtained by recrystallization of the D-salt from MeOH.

EXAMPLE 22

Resolution of (D,L) pHPGpTS by addition of Phenyl Glycine (PG)

350 mg D,L-pHPGpTS and 24 mg phenyl glycine (PG) (i.e., 6.8% based on the mixture of D,L-pHPGpTS) were slurried in 1 cc 0.5M p-toluene sulphonic acid and treated as in example 15. After 2 hours the supersaturated solution was seeded with 1 mg L-pHPGpTS. After 1 additional hour, the resulting crystals were collected by filtration. The enantiomeric excess was 80.2% and the yield 19.4%.

Additional examples of resolution of pHPGpTS by addition of PG or pMPG in 15 weight % of the initial D,L-pHPG are given in Table IV below:

TABLE IV

| Example | (D,L)pHPGpTS (mg/cc) | Additive | Conditions | Purified Product e.e. | Yield |
|---|---|---|---|---|---|
| 23 | 350 | D-PG | seeds, (D,L) room temp. | 78 | 17.5 |
| 24 | 350 | D-PMPG | seeds (D, L) room temp. | 69 | 12.3 |
| 25 | 350 | D-PMPG | seeds (L) room temp. | 80 | 16.3 |

EXAMPLE 26

1 g D,L-GLU.H$_2$O and 200 mg L-LYS.HCl were slurried in 5 ml 5N HCl and heated to about 60° C. until complete dissolution occurred. The solution was filtered, cooled to room temperature, and about 0.5 mg seed crystals of D,L-GLU.HCl added. After one day of standing without agitation, 229 mg crystals had formed, and these were separated by decantation and dried. The specific rotation of these product crystals was $[\alpha]_D^{25} = -24.2°$ (c=5, HCl 1N), corresponding to an enantiomeric excess of 98.4% D-GLU in an overall yield of 20.7% with respect to the initial D,L-GLU introduced.

EXAMPLES 27-30

In a manner similar to Example 26, experiments were performed also at room temperature in 5N HCl in the presence of L-LYS.HCl and seeds of D,L-GLU.HCl but in different conditions. The results are given in Table V below:

TABLE V

Resolution of D, L-GLU.HCl in the presence of L-Lys.HCl

| Example | wt. of D, L-GLU.HCl in 5 ml 5N HCl (g) | wt. LYS.HCl (mg) | Time (days) | Precipitated crystals e.e. | overall yield |
|---|---|---|---|---|---|
| 27 | 1 | 25 | 1 | 96.3 | 14.8 |
| 28 | 1 | 200 | 1 | 90.2 | 22.6 |
| 29 | 1.6 | 333 | 4 | 100 | 20.8 |
| 30 | 1 | 800 | 10 | 99.1 | 20.2 |

EXAMPLE 31

1 g. D,L-GLU.H$_2$O and 100 mg L-ornithine HCl (i.e., 10% based on the mixture of D,L-GLU.H$_2$O) were slurried in 5 cc HCl 5N, and the slurry heated util complete dissolution occurred. The supersaturated solution was filtered, cooled to room temperature, about 0.5 mg D,L-GLU.HCl crystals were added.

After standing of the solution 2 days without agitation, 196 mg of crystals precipitated, which were separated by decantation and dried. The specific rotation of these crystals was $[\alpha]_D^{25} = -24.6°$ (C=5, HCl 1N), corresponding to an enantiomeric excess of 100% of D-GLU in a yield of 17.6% with respect to the initial D,L-GLU introduced.

EXAMPLES 32-35

In a manner similar to example 31, experiments were performed also at room temperature, with 1 g, D,L-GLU.H$_2$O in 5 cc HCl 5N, in the presence of seeds of D,L-GLU.HCl and variable amounts of L-ORN.HCl. The results are given in Table VI below.

TABLE VI

Resolution of D, L-GLU.HCl in the presence of L-ORN.HCl

| Example | wt L-ORN.HCl (mg) | time (days) | Precipitated crystals e.e. | Yield |
|---|---|---|---|---|
| 32 | 50 | 2 | 87.4 | 21.15 |
| 33 | 200 | 3 | 98.8 | 17.1 |
| 34 | 200 | 14 | 92.8 | 19.5 |
| 35 | 500 | 10 | 98.4 | 20.4 |

EXAMPLE 36

1 g. D,L-GLU.H$_2$O and 25 mg L-HIS.HCl (i.e., 2.5% based on the mixture of D,L-GLU.H$_2$O) were slurried in 5 ml HCl 5N and treated as in example 31. After 2 days 517 mg of a mixture of big well shaped bars and thin powdery plates had precipitated. These were decanted and dried. The overall mixture was racemic. The two morphological forms were then separated mechanically: the bars had a specific rotation of $[\alpha]_D^{25} = -22.9$ (c=5, HCl 1N) corresponding to an enantiomerical purity of 93.1%. D-GLU, while the plates had $[\alpha]_D^{25} = +24$, corresponding to 97.6% pure L-GLU.

EXAMPLES 37-42

In a manner similar to example 31 experiments were performed, also at room temperature, with 1 or 1.5 g D,L-GLU.H$_2$O in 5 cc HCl 5N, in the presence of seed crystals of D,L-GLU.HCl and of different additives in solution. The results are given in Table VII below:

TABLE VII

Resolution of D, L-GLU.HCl in the presence of various additives

| Example | wt D, L-GLU.H$_2$O (g) | Additive | wt additive (g) | time (days) | precipitated crystals e. e. | yield |
|---|---|---|---|---|---|---|
| 37 | 1 | L-HIS.HCl | 0.5 | 14 | 96.1 | 21.8 |
| 38 | 1 | " | 0.8 | 14 | 99.2 | 20.3 |
| 39 | 1.5 | " | 0.8 | 6 | 94 | 24.5 |
| 40 | 1 | L-CYS.HCl | 0.8 | 2 | 99.2 | 16.9 |
| 41 | 1 | L-THR | 0.5 | 18 | 96.3 | 8.2 |
| 42 | 1 | L-SER | 0.2 | 4 | 58.5 | 3.3 |

We claim:

1. A process for the resolution of a mixture of D- and L-forms of p-hydroxyphenylglycine p-toluene sulfonate, whereby the ratio of one desired enantiomorph to the other undesired enantiomorph of said p-hydroxyphenylglycine p-toluene sulfonate is increased in the crystalline compound obtained, as compared to the ratio in the starting material, which process comprises:

forming a supersaturated solution of said mixture;

adding, as a crystallization inhibitor, a small amount of another predetermined amino acid having a molecular structure which resembles that of one of the enantiomorphs of said racemic mixture, said crystallization inhibitor being a D-amino acid to inhibit the growing of D-amino acid when the L-amino acid is desired, or an L-amino acid when the D-amino acid is desired; and crystallizing a portion of the p-hydroxyphenylglycine p-toluene sulfonate from said supersaturated solution.

2. A process in accordance with claim 1, wherein said crystallization inhibitor is an amino acid selected from the group consisting of tyrosine, tyrosine p-toluene sulfonate, dopa, dopa p-toluene sulfonate, α-methyldopa, α-methyldopa p-toluene sulfonate, phenylalanine, phenylalanine p-toluene sulfonate, phenylglycine, phenylglycine, p-toluene sulfonate, p-methyloxyphenylglycine, and p-methoxyphenylglycine p-toluene sulfate.

3. A process in accordance with claim 2, wherein said adding step further includes adding seeds of p-hydroxyphenylglycine p-toluene sulfonate of the desired form to said supersaturated solution.

4. A process for the resolution of a mixture of D- and L-forms of threonine, whereby the ratio of one desired enantiomorph to the other undesired enantiomorph of said threonine is increased in the crystalline compound obtained, as compared to the ratio in the starting material, which process comprises:

forming a supersaturated solution of said mixture;

adding, as additive, the D-form of an amino acid selected from the group consisting of glutamic acid, aspartic acid, glutamine, asparagine and cystein when the L-form of threonine is desired, or adding, as additive, the L-form of one of said amino acids when the D-form of threonine is desired; and crystallizing a portion of the threonine from said supersaturated solution.

5. A process in accordance with claim 4, wherein said adding step further includes adding seeds of threonine of the desired form to said supersaturated solution.

6. A process according to claim 1, wherein the additive is added in an amount of 1 to 15 weight % calculated on the mixture of the D- and L-forms.

7. A process according to claim 1, wherein the additive is added in an amount of 1 to 10 weight % calculated on the mixture of the D- and L-forms.

8. A process according to claim 1, wherein the additive is added in an amount of 1 to 5 weight % calculated on the mixture of the D- and L-forms.

* * * * *